(12) United States Patent
Murigneux et al.

(10) Patent No.: US 8,686,231 B2
(45) Date of Patent: Apr. 1, 2014

(54) MAIZE WITH INCREASED TOLERANCE TO FUNGAL DISEASES

(75) Inventors: Alain Murigneux, La Roche Blanche (FR); Jean-Pierre Martinant, Vertaizon (FR); Christophe Tatout, Salt en Donzy (FR); Bruno Grezes-Besset, Cornebarrieu (FR)

(73) Assignee: Biogemma, Paris (FR)

( * ) Notice: Subject to any disclaimer, the term of this patent is extended or adjusted under 35 U.S.C. 154(b) by 524 days.

(21) Appl. No.: 12/743,921

(22) PCT Filed: Nov. 19, 2008

(86) PCT No.: PCT/EP2008/065850
§ 371 (c)(1),
(2), (4) Date: May 24, 2011

(87) PCT Pub. No.: WO2009/065863
PCT Pub. Date: May 28, 2009

(65) Prior Publication Data
US 2011/0252500 A1    Oct. 13, 2011

(30) Foreign Application Priority Data
Nov. 22, 2007    (FR) .................................... 07 08180

(51) Int. Cl.
*A23K 3/02* (2006.01)
*A01H 5/00* (2006.01)
*A01H 1/00* (2006.01)
*C12N 15/87* (2006.01)

(52) U.S. Cl.
USPC ........ 800/301; 800/320.1; 800/291; 800/279; 800/265

(58) Field of Classification Search
None
See application file for complete search history.

(56) References Cited

U.S. PATENT DOCUMENTS

| 8,115,054 B2 | 2/2012 | Tatout et al. |
| 8,330,006 B2 | 12/2012 | Murigneux et al. |
| 2005/0086716 A1 | 4/2005 | Rogowsky et al. |

FOREIGN PATENT DOCUMENTS

| FR | 2833615 A1 | 6/2003 |
| WO | WO-99/10498 A2 | 3/1999 |
| WO | WO-01/34817 A2 | 5/2001 |
| WO | WO-03/008585 A2 | 1/2003 |
| WO | WO-03/054229 A2 | 7/2003 |
| WO | WO-2006/035045 A1 | 4/2006 |

OTHER PUBLICATIONS

Guillet-Claude et al. 2004. Genetic diversity associated with variation in silage corn digestibility for three O-methyltransferase genes involved in lignin biosynthesis. Theor. Appl. Genet. 110(1):126-135.*
Database: EMBL, Accession No. AJ242981, Zea mays mRNA for Caffeoyl CoA O-methyltransferase (ccoAOMT gene), Nov. 2, 2007.
Database: EMBL, Accession No. AY279016, Zea mays F7025 caffeoyl CoA 3-O-methyl-transferase (ccoaomt2) gene, complete cds, Jan. 29, 2005.
Guillet-Claude, C., et al., "Genetic diversity associated with variation in silage corn digestibility for three O-methyltransferase genes involved in lignin biosynthesis," Theor Appl Genet, 2004, vol. 110, pp. 126-135.
English language translation of WO 03/254229, Jul. 3, 2003.

* cited by examiner

*Primary Examiner* — Anne Kubelik
*Assistant Examiner* — Jeffrey Bolland
(74) *Attorney, Agent, or Firm* — Novak Druce Connolly Bove + Quigg LLP

(57) ABSTRACT

The present invention relates to the field of improving the digestibility of maize and the tolerance of maize to fungal pathogens, and in particular to *Fusarium* disease, by introgression of the G2092 allele.

10 Claims, 1 Drawing Sheet

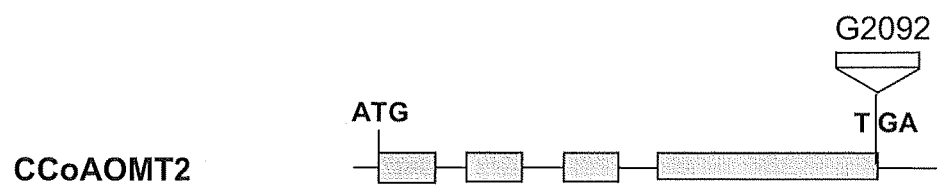

SEQUENCE LISTING

<160> NUMBER OF SEQ ID NOS: 5

<210> SEQ ID NO 1
<211> LENGTH: 1463
<212> TYPE: DNA
<213> ORGANISM: Zea mays

<400> SEQUENCE: 1

| | | | | | |
|---|---|---|---|---|---|
| cgcaagccag | tgccgcgccc | agatctccgc | gacagatcag | tcgttcgtcc | agctaactgc | 60 |
| actgcacgca | atggccacca | cggcgaccga | ggcgaccaag | acgactgcac | cggcgcagga | 120 |
| gcagcaggcc | aacggcaacg | gcaacggcaa | cggcgagcag | aagacgcgcc | actccgaggt | 180 |
| cggccacaag | agcctgctca | agagcgacga | cctctaccag | gtaaacaagc | tgggcgcaat | 240 |
| gaatggctga | atctgaccgg | gatccgagtc | tctgaccgcg | ggggagaat | gatccgcagt | 300 |
| acatcctgga | cacgagcgtg | tacccgcggg | agccggagag | catgaaggag | ctgcgcgaga | 360 |
| tcaccgccaa | gcacccatgg | tatgtcccgc | tagcttttcg | cctgtcgtac | gtggtggatt | 420 |
| cgagtgtgtg | ggcctgctgg | acgacagacc | gagatctgac | tgagaagtga | gaacatggct | 480 |
| tggcgtgcag | gaacctgatg | accacctccg | ccgacgaggg | ccagttcctc | aacatgctca | 540 |
| tcaagctcat | cggcgccaag | aagaccatgg | agatcggcgt | ctacaccggc | tactcgctcc | 600 |
| tcgccaccgc | gctcgcactc | ccggaggacg | gcacggtcgg | tctctctctc | tctctctctc | 660 |
| tctcccagat | ctgccaccca | cccacccacc | tccggtccac | tggtacgccc | atgatcttta | 720 |
| cccttctctc | tctctgtctc | tctgttgctc | gccccccgc | agatcttggc | catggacatc | 780 |
| aaccgcgaga | actacgagct | aggccttccc | tgcatcgaca | aggccggcgt | ggcccacaag | 840 |
| atcgacttcc | gcgagggccc | cgcgctcccc | gtcctggacg | acctcgtggc | ggacaaggag | 900 |
| cagcacgggt | cgttcgactt | cgccttcgtg | gacgccgaca | aggacaacta | cctcagctac | 960 |
| cacgagcggc | tcctgaagct | ggtgagggcc | ggcggcctca | tcggctacga | caacacgctg | 1020 |
| tggaacggct | ccgtcgtgct | ccccgacgac | gcgcccatgc | gcaagtacat | ccgcttctac | 1080 |
| cgcgacttcg | tcctcgccct | caacagcgcg | ctcgccgccg | acgaccgcgt | cgagatctgc | 1140 |
| cagctccccg | tcggcgacgg | cgtcacgctc | tgccgccgcg | tcaagtgaaa | aaagaaaga | 1200 |
| aaaaaaaac | acacataccc | tgcgttcctg | ctgcccccgg | ctccgtctgg | ccccaccgc | 1260 |
| caccgacggc | ggcgccgcac | ccccgttcc | aatcatatcg | tagacgacgc | gcagcattaa | 1320 |
| attatcaatc | accggctctg | gctctttctt | ggccctgtac | tgtactacta | tactaatgtc | 1380 |
| ccttcttgtt | ttttttcttt | gggaattgtc | gccgtttcag | tatacgtaaa | atctcgatgt | 1440 |
| cgataataca | gtactactac | caa | | | | 1463 |

<210> SEQ ID NO 2
<211> LENGTH: 1167
<212> TYPE: DNA
<213> ORGANISM: Zea mays

<400> SEQUENCE: 2

| | | | | | |
|---|---|---|---|---|---|
| cgcaagccag | tgccgcgccc | agatctccgc | gacagatcag | tcgttcgtcc | agctaactgc | 60 |
| actgcacgca | atggccacca | cggcgaccga | ggcgaccaag | acgactgcac | cggcgcagga | 120 |
| gcagcaggcc | aacggcaacg | gcaacggcga | gcagaagacg | cgccactccg | aggtcggcca | 180 |
| caagagcctg | ctcaagagcg | acgacctcta | ccagtacatc | ctggacacga | gcgtgtaccc | 240 |
| gcgggagccg | gagagcatga | aggagctgcg | cgagatcacc | gccaagcacc | catggaacct | 300 |

```
gatgaccacc tccgccgacg agggccagtt cctcaacatg ctcatcaagc tcatcggcgc    360
caagaagacc atggagatcg gcgtctacac cggctactcg ctcctcgcca ccgcgctcgc    420
actcccggag gacggcacga tcttggccat ggacatcaac cgcgagaact acgagctagg    480
ccttccctgc atcaacaagg ccggcgtggg ccacaagatc gacttccgcg agggccccgc    540
gctccccgtc ctggacgacc tcgtggcgga caaggagcag cacgggtcgt tcgacttcgc    600
cttcgtggac gccgacaagg acaactacct caactaccac gagcggctcc tgaagctggt    660
gaggcccggc ggcctcatcg gctacgacaa cacgctgtgg aacggctccg tcgtgctccc    720
cgacgacgcg cccatgcgca agtacatccg cttctaccgc gacttcgtcc tcgccctcaa    780
cagcgcgctc gccgccgacg accgcgtcga gatctgccag ctccccgtcg gcgacggcgt    840
cacgctctgc cgccgcgtca agtgaaaaaa agaaagaaaa aaaaaacaca catacccgtc    900
gttcctgctg ccccggctc cgtctggccc ccaccgccac cgacggcggc gccgcacccc    960
ccgttccaat catatcgtag acgacgcgca gcattaaatt atcaatcacc ggctctggct   1020 cttcttggc cctgtactgt actactatac taatgtccct tcttgttttt ttttcttggg   1080
aattgtcgcc gtttcagtat acgtaaaatc tcgatgtcga taatacagta ctactaccaa   1140
tttaactaaa aaaaaaaaa aaaaaaa                                        1167

<210> SEQ ID NO 3
<211> LENGTH: 18
<212> TYPE: DNA
<213> ORGANISM: Artificial
<220> FEATURE:
<223> OTHER INFORMATION: Synthetic primer CCoA2-intspe-21

<400> SEQUENCE: 3
gacctcgtgg cggacaag                                                   18

<210> SEQ ID NO 4
<211> LENGTH: 20
<212> TYPE: DNA
<213> ORGANISM: Artificial
<220> FEATURE:
<223> OTHER INFORMATION: Synthetic primer CCoA2_16

<400> SEQUENCE: 4
ccaagaaaga gccagagccg                                                 20

<210> SEQ ID NO 5
<211> LENGTH: 25
<212> TYPE: DNA
<213> ORGANISM: Artificial
<220> FEATURE:
<223> OTHER INFORMATION: Synthetic primer OMuA

<400> SEQUENCE: 5
cttcgtccat aatggcaatt atctc                                           25
```

MAIZE WITH INCREASED TOLERANCE TO FUNGAL DISEASES

RELATED APPLICATIONS

This application is a national stage application (under 35 U.S.C. §371) of PCT/EP2008/065850, filed Nov. 19, 2008, which claims benefit of French application 0708180, filed Nov. 22, 2007.

The present invention relates to the field of improving maize, in particular improving the digestibility of maize, and the tolerance of maize to fungal pathogens, and in particular to *Fusarium* disease.

The present invention relates more precisely to the development of a particular allele of the CCoAOMT2 gene in maize. The consequence of the presence of this allele is an improvement in the digestibility (increased digestibility) and the tolerance to *Fusarium* disease compared to an isogenic maize not possessing the allele. The quantity of lignin present in the plant is also reduced.

Lignin is one of the two major components of the plant wall with cellulose. The plant wall mainly consisting of cellulose, hemicellulose and lignin offers the cell a natural barrier against the exterior. Numerous studies have shown that one of the responses to biotic stress (pathogenic attacks) or abiotic stress (drought, wind, etc) consists in a strengthening of the plant wall, in particular in a higher content of lignin. Moreover, the yields of numerous agronomic or industrial sectors are directly linked to the content and/or composition of lignin in the wall, especially the paper industry, the production of fuels (in particular the biomass intended for biofuels) or the production of silage.

For example, it is possible to improve the quality of silage maize by reducing the content of lignin or by modifying the composition thereof. Maize silage is a valuable feed: the yield in the field is relatively high, harvesting and storage are easy, the nutritional qualities are stable and can easily be supplemented with proteins by other fodder silages or by soya oil cakes. An experiment carried out by Emile (1995, Annales de zootechnie) demonstrates that feeding livestock with a more digestible maize makes it possible to increase the daily milk production and the weight gain compared with feeding stuff containing a less digestible maize. The optimization of the qualities of maize silage thus consists in increasing the net energy provided by this type of feeding stuff by improving its digestibility and therefore by reducing the content of lignin.

Accordingly, the selection or production of more digestible maize plants, in particular whose lignin biosynthesis pathway is modified, is one of the preferred routes for improving maize. It is however advantageous for the selected plants to have good yields and not to be very sensitive to various stresses (mechanical, hydric, etc).

Moreover, maize crops are subject to attacks by numerous pathogens. Among these, mention may be made of viruses, bacteria, but also fungal pathogens, which are responsible for numerous diseases, and sometimes for the presence of mycotoxins.

Accordingly, maize may be attacked by fungi responsible for *Fusarium* diseases (due to *Fusarium*, including *F. roseum, F. gramninearum, F. liseola, F. moniliforme*), smut (common or head smut, due to *Ustilago zeae, Ustilago maydis*), anthracnose (*Colletotrichum graminicola*), kabatiellosis, helminthosporiosis (*Helminthosporium turcicum*), rust (*Puccinia maydis*), mildew. In general, fungal attacks are responsible for desiccation and/or rot of plants, which are located variously according to the pathogen.

Fungi of the genus *Fusarium* are responsible for *Fusarium* disease. Mention may be made of the species *F. graminearum* and *F. moniliforme*, which are maize pathogens and whose importance varies according to the climatic conditions and the earliness of the maize varieties. A distinction may be made between *Fusarium* disease of the cob and *Fusarium* disease of the stem, the infectious processes being very different. Certain pathogenic agents are nevertheless common to both types of *Fusarium* disease. Several modes of contamination of the plant by fungus are known, such as the penetration of the infectious mycelium into the plant by lesions attributable to insects and to birds, or the direct penetration at the level of the cob silk, resulting in the infection of the grains. In the case of *Fusarium* disease of the stem, the contamination may also occur via the seeds or more rarely the roots.

*Fusarium* disease of the cob, which causes destruction of the grains, reduces the yield of the maize crops. The pathogenic agents implicated are moreover very damaging because they cause the accumulation, in grains whether or not destroyed, of various mycotoxins (Zearalenone, Deoxynivalenol, Fumonisins) which exhibit varying levels of toxicity according to the animal species and which are difficult to eliminate.

Fungicidal treatments are difficult to use and have only a limited effect on *Fusarium*. The best way of combating *Fusarium* disease of the cob is the use of genetic resistance. Few hybrids currently have such a resistance, which, when it exists, is a partial resistance which remains moderate.

It therefore seems important to identify methods for increasing the tolerance to fungal diseases in maize.

The present application shows that the presence of the 62092 allele of the maize CCoAOMT2 gene makes it possible to obtain a maize that is more digestible and that exhibits better tolerance to fungal diseases, and in particular to *Fusarium* disease. This maize also exhibits resistance to fungal diseases caused by fungal pathogens such as those described above.

The G2092 allele is an insertion mutant in the CCoAOMT2 gene of the phenylpropanoid pathway, and more particularly the lignin biosynthesis pathway. This phenylpropanoid pathway leads, starting with phenylalanine, to the synthesis of a wide variety of substances such as anthocyanins, isoflavonoids, stilbenes, hydroxycinnamic acid esters, or to lignin. Lignin is responsible for the stiffness of the cell walls and for impermeability of the conductive tissues.

Caffeoyl Coenzyme-A O-Methyl Transferase (CCoAOMT) is an important enzyme in the pathway for the biosynthesis of monolignols and more particularly of the G subunits. CCoAOMT appears to play a role during several stages of the lignin biosynthesis pathway. Accordingly, it is thought to be involved in an alternative methylation pathway of lignin biosynthesis in zinnias, and the methylation pathway mediated by CCoAOMT is thought to be probably one of the general lignin biosynthesis pathways during plant growth and development.

In maize, two genes encode CCoAOMT: the CCoAOMT1 gene (GenBank AJ242980), located on chromosome 6 and the CCoAOMT2 gene (GenBank AJ242981, SEQ ID No. 2), located on chromosome 9.

Patent applications WO9910498 and WO0134817 relate, inter alia, to the maize CCoAOMT1 gene.

In application WO 03/054229, the inventors demonstrated the colocalization of the CCoAOMT2 gene, located on chromosome 9, with a QTL for digestibility and a QTL for lignin content of the walls. They additionally identified mutations of the CCoAOMT2 gene creating polymorphic alleles associated with maize digestibility. The use of the allelic variation of CCoAOMT2 to control the digestibility of silage maize is also described in Guillet-Claude et al (Theor Appl Genet. 2004 December; 110(1): 126-35).

The object of the present invention is to provide persons skilled in the art with maize which indeed has improved digestibility and increased tolerance to fungal pathogens, by developing a favorable allele of CCoAOMT2 (called G2092), the insertion of a transposon having been carried out after nucleotide 1186 in the gene represented by SEQ ID No. 1, which corresponds to the genomic DNA for this enzyme. The application also describes a method for obtaining a maize which has increased tolerance to a fungal pathogen, comprising the introgression of the G2092 allele thus identified into said maize.

The sequence of a cDNA (GenBank AJ24981) is represented by SEQ ID No. 2, the encoding part extending from nucleotides 70 to 865 for this sequence. It is clear that these sequences are given only by way of examples, and that persons skilled in the art are themselves capable of identifying the genomic and/or mRNA sequences of CCoAOMT2 for different maize varieties, in particular in the GenBank database (sequences AY279004 to AY279035) or in Guillet-Claude et al (2004, op. cit.).

The maize according to the invention exhibits a quantitative and/or qualitative alteration of the synthesis of lignin, and a better tolerance to fungal pathogens.

The expression "quantitative alteration of the synthesis of lignin" is understood to mean a decrease in the quantity of lignin in the modified maize according to the invention compared with a normal maize (unmodified control according to the invention), evaluated, for example by measuring the Klason lignin or acid detergent lignin according to methods well known to a person skilled in the art (see for example Jung et al., J Agric Food Chem. 1999 May; 47(5):2005-8; Jung et al, J Dairy Sci. 1997 August; 80(8):1622-8).

The expression "qualitative alteration of the synthesis of lignin" is understood to mean a modification in the composition of the lignin of the modified plant according to the invention compared with a control plant (unmodified according to the invention), for example a variation in the S/G subunits ratio, or a modification of the quality of ferulic acid. The methods for the qualitative analysis of lignin are also known in the art. NMR may be mentioned in particular.

Among the fungal pathogens, mention may be made in particular of the genus *Fusarium*, preferably chosen from *F. graminearum, F. liseola, F. roseum* and *F. moniliforme*. The maize also exhibits tolerance to the other fungal pathogens cited above and in particular to the pathogens of the genus *Helminthosporium*, in particular *H. turcicum*.

Seeds having the G2092 allele have been deposited at NCIMB Limited, Ferguson Building, Craibstone Estate, Bucksburn, Aberdeen, Scotland, AB21 9YA, UK, on Nov. 14, 2007, according to the provisions of the Budapest Treaty, under the number NCIMB 41518.

The invention relates in particular to a maize plant, or a maize grain having said G2092 allele.

The invention also relates to a maize or a maize grain having both the G2092 allele and an allele of the CCR1 gene, called Δ3318, said Δ3318 allele being present in a representative sample of seeds deposited at NCIMB under the number NCIMB 41236 on Jul. 23, 2004, according to the provisions of the Budapest Treaty. This Δ3318 allele is described in patent application WO 2006/035045.

The invention also relates to a maize or a maize grain having both the G2092 allele and an allele of the C4H gene, called D1938, said D1938 allele being present in a representative sample of seeds deposited at NCIMB under the number NCIMB 41507 on Oct. 15, 2007, according to the provisions of the Budapest Treaty.

The invention also relates to a maize or a maize grain having at the same time the G2092 allele, the allele of the CCR1 gene called 43318 and the allele of the C4H gene called D1938.

Preferably, the maize according to the invention is an "elite" maize. The person skilled in the art knows well the definition of an elite maize. The expression elite maize is understood to mean a maize intended to generate hybrids intended to be marketed by crossing with another elite maize. An elite maize is defined as such in relation to the region envisaged for the marketing, and the desired agronomic character(s) for the hybrid progeny. It is in particular a maize which may be registered in a reference catalog.

Accordingly, depending on whether the progeny is intended as foodstuff for humans or animals, a grain yield or a yield per hectare and a good digestibility are sought respectively, for example, when the "elite maize" nature is evaluated.

In order to determine the elite character of a maize, a comparison is made between the hybrids obtained therefrom and the reference commercial hybrids (sold for the same objective in the same region), using field trials, by recording and measuring the agronomic characters appropriate for the desired objective. A maize is defined as elite if the results obtained, parameters studied for a hybrid obtained by crossing of said maize are greater than 90% of the results recorded for the same reference hybrid parameters.

Accordingly, an elite maize is a maize that has the maximum number of agronomic characteristics necessary for an economic penetration of the target market. Given that the maize market is nowadays a market of hybrids, the evaluation of the elite character of a maize is also made by the capacity of said maize for combination/production of hybrids.

Accordingly, the present invention relates preferentially to an elite maize intended for the marketing of hybrids as animal feed and silage, having the G2092 allele. This elite maize is therefore homozygous for the G2092 allele.

In another embodiment, the invention relates to a hybrid maize obtained by crossing two homozygous parental lines, said hybrid maize having a G2092 allele. This hybrid maize may be homozygous (if each homozygous parent has the G2092 allele) or heterozygous for the G2092 allele.

The invention also relates to a maize or maize grain containing one or more transgenes in addition to the G2092 allele. Mention may be made of transgenes conferring male sterility, male fertility, resistance to a herbicide (in particular glyphosate, glufosinate, imidazolinone, sulfonylurea, L-phosphinotricin, triazine, benzonitrile), resistance to insects (in particular a transgene encoding a *Bacillus thuringiensis* toxin), tolerance to hydric stress. These maize plants may be obtained by crossing a maize containing the G2092 allele with a maize containing said transgene. The use of backcrossings followed by self-fertilization makes it possible to obtain an elite maize that is homozygous for the G2092 allele and the transgene. However, a hybrid maize containing both the G2092 allele and the transgene is also within the scope of the invention.

The present invention also provides persons skilled in the art with the means which make it possible to select maize plants having improved characteristics of tolerance to fungal pathogens. Indeed, PCR, or Southern blotting (hybridization of genomic DNA to membranes) simply has to be carried out in order to monitor the presence of the insertion in the last exon of the gene encoding CCoAOMT2. Persons skilled in the art can easily determine the primers and probes which make it possible to identify the presence of the G2092 allele. The invention thus also relates to a method for monitoring the G2092 allele by molecular biology techniques, and in particular by PCR using the primers mentioned in the examples.

The subject of the invention is also a method for producing maize plants exhibiting improved tolerance to fungal pathogens by virtue of the G2092 allele.

The invention also relates to a method for producing a maize line exhibiting better tolerance to fungal diseases, comprising the step of introgression of the G2092 allele, into a reference line, exhibiting an agronomic character of quality. The introgression of the character is made in particular by selection, according to methods known in the art (crossings and self-fertilization). The plants are selected in particular by means of molecular markers.

The principle thereof is stated below:

A series of backcrosses between the elite line and the line carrying the G2092 allele are carried out.

During the backcrosses, it is possible to select the individuals carrying the G2092 allele, and which have recombined the smallest fragment of the donor line around this allele. Indeed, using molecular markers, the individuals which have the genotype of the elite line, for the markers close to the gene, are selected.

Furthermore, it is also possible to accelerate the return to the elite parent using the molecular markers distributed over the entire genome. At each backcross, the individuals having the most fragments derived from the recurrent elite parent will be chosen.

With a good implementation, from the fourth generation, it is possible to obtain a near-isogenic line of the elite line, that is to say identical to the starting elite line, but which has integrated the locus carrying the G2092 allele.

In a first embodiment of the invention, for maize, this relates to a method for producing a maize exhibiting tolerance to fungal pathogens, consisting in:
a) crossing a first maize line having the G2092 allele with a second maize line not having said allele,
b) genotyping the progeny obtained and selecting the descendants having the G2092 allele with the best genome ratio with regards to said second line,
c) backcrossing said descendants with said second maize line,
d) repeating, if necessary, steps b) and c) until an isogenic line is obtained from said second maize line, having the G2092 allele,
e) optionally, carrying out self-fertilization in order to obtain a plant homozygous for the G2092 allele.

In another embodiment, the invention relates to a method for producing a maize exhibiting increased digestibility, comprising the introgression of the G2092 allele into said maize, comprising the steps consisting in:
a) crossing a first maize line having the G2092 allele with a second maize not having said allele,
b) genotyping the progeny obtained and selecting the descendants having the G2092 allele with the best genome ratio as regards said second maize,
c) backcrossing said descendants with said second elite maize line which can be used for the production of hybrids,
d) repeating, if necessary, steps b) and c) until an isogenic line is obtained from said second maize, having the G2092 allele,
e) optionally, carrying out self-fertilization in order to obtain a plant homozygous for the G2092 allele.

The genotyping of step b) is preferably carried out using molecular markers (for example microsatellite markers), making it possible to define the contribution of each of the two parents to the progeny. Maize plants which possess the appropriate genetic character as regards the G2092 allele, are also selected from the progeny, in a conventional manner by molecular biology methods (such as PCR or Southern blotting).

The increased tolerance and/or digestibility of the maize according to the present invention are in comparison with a near-isogenic maize not comprising the G2092 allele.

Surprisingly, it has been shown that repeating the backcrossings between the lines selected in step b) and the second maize makes it possible to obtain the appearance of a considerably more marked phenotype within said second maize. Moreover, it is surprising to observe such a phenotype even though the insertion is located in the stop codon of the gene encoding CCoAOMT2, and even though the protein should therefore be produced and operational.

The invention also relates to a method in which the Δ3318 allele is also introgressed into the maize into which the G2092 allele is introgressed. The introgression of the Δ3318 is carried out in particular according to the teachings of WO 2006/035045, using in particular the primers described in the examples of this application.

The introgression of the D1938 allele may also be envisaged in parallel with the introgression of the G2092 allele or of the two alleles G2092 and D1938.

Moreover, the agronomic results observed after multiple backcrosses (5 backcrosses and 2 self-fertilizations) do not show any difference between the isogenic lines exhibiting the mutation and the control plants.

Finally, the invention relates to the use of a maize according to the invention, for the preparation of a composition intended as animal feed, to a method for the preparation of a composition intended as animal feed comprising silage from a maize according to the invention, and therefore to the composition intended as animal feed thus obtained. In particular, said maize is particularly useful as livestock feed.

DESCRIPTION OF THE FIGURES

FIG. 1: schematic representation of the insertion of the Mutator transposable element in the last exon of the CCoAOMT2 gene. The shaded blocks correspond to the exons, the lines correspond to the introns.

EXAMPLES

Example 1

Identification of a Maize Having an Insert in the CCoAOMT2 Gene

A maize line having an insertion of a transposable element at position 1186 of the reference sequence SEQ ID No. 1 is isolated (FIG. 1). The allele thus obtained is named G2092.

The insert of the transposable element is located in the triplet TGA (encoding the stop codon of the CCoAOMT2 protein) in the last exon of the CCoAOMT2 gene (FIG. 1). It is possible that this insertion affects the conformation and/or stability of the mRNA.

In order to determine if the insertion is in homozygous or heterozygous form, a pair of primers was defined: sense primer CCoA2-intspe-21 of sequence SEQ ID No. 3: GAC-CTCGTGGCGGACAAG and an antisense primer CCoA216 of sequence SEQ ID No. 4: CCAAGAAAGAGCCA-GAGCCG.

In addition to these two primers, the primer OMuA (SEQ ID No. 5): CTTCGTCCATAATGGCAATTATCTC specific to the endogenous transposable element is used. This primer is directed toward the end of the transposon.

These three primers may be used simultaneously in a PCR amplification experiment starting with genomic DNA (hybridization temperature=58° C.). Deposition on gel of the amplification products reveals:
- the production of a single band about 500 bp long for so-called "wild-type" plants at this locus (that is to say having no mutation);
- production of two bands of about 200 bp and 400 bp for mutant homozygous plants, corresponding to the amplifications obtained with the primers present in the gene and in the transposon (because of the insertion, the amplification with the primers CCoA2-intspe-21 and CCoA2__16 is impossible because it is too long);
- or the production of all the three bands for the heterozygous plants.

Example 2

Phenotype Analysis of the G2092 Mutant for the Resistance to Fungal Disease Character A homozygous mutant plant and a wild homozygous control are available for each insertion event. Given the advanced stages of introgression of the mutation, it is possible to consider that the mutant and the wild type differ only in the presence or otherwise of the mutation. The experiment is carried out according to the following protocol:
2 sites
3 repeats per site
Artificial inoculation of *Fusarium moniliforme*
Notation of the symptoms observed on the cobs (note from 1 to 7). It is a visual notation of intensity of attack on the cob: the note for intensity of attack is calculated from the percentage of the surface area of the cob attacked by the pathogen (Reid et al Agriculture and Agri-Food Canada, Ottawa, Ont. Technical Bulletin 1996-5E. 40 pp). The notes correspond to: 1=0% attacked; 2=1-3%; 3=4-10%; 4=11-25%; 5=26-50%; 6=51-75%; 7=76-100%
Optionally assaying of the mycotoxins (fumonisins)

In the examples below, the "sites" repeats were converted to "single repeats" so as to carry out a single statistical analysis.

The statistical analysis was carried out on each mutant so as to know if there is a difference between mutant (M) and wild-type or control (S).

The results demonstrate that the insertion of a transposon into the CCoAOMT2 gene, involved in the pathway for the metabolism of phenylpropanoids and lignin, increases tolerance to infection by *Fusarium moniliforme*. This effect is reproducible depending on the sites of cultivation.

Mutant G2092_CCoAOMT2

| Type | Number | Mean values | Standard deviation |
|---|---|---|---|
| M | 81 | 3.07471 | 0.129118 |
| S | 103 | 3.71153 | 0.114828 |

| Contrast | Difference | +/−limits |
|---|---|---|
| M − S | *−0.636821 | 0.341066 |

*statistically significant difference

Mutant More Resistant than the Wild Type; Moderate Effect

Example 3

Phenotype Analysis of the G2092 Mutant for the Digestibility Character

In order to study more precisely the effect of the insertion observed in the CCoAOMT2 gene in an elite maize, successive backcrosses are carried out with an elite maize line.

This method very rapidly makes it possible to obtain near-isogenic lines which differ only in the locus carrying the modified allele, the descendants being tested for having a genome ratio that is as close as possible to that of the elite parent while having the allele which it is desired to introgress. These tests are assisted by molecular markers (well known techniques, microsatellites, AFLP, etc). To try to assess the effect of the insertion as early as possible (production of homozygous plants), self-fertilizations are carried out at the different intermediate stages of backcrossing.

The introgression of the G2092 allele makes it possible to obtain a reduction in the quantity of lignin (Acid Detergent Lignin) after isolation of the walls (Neutral Detergent Fibers), according to methods known to a person skilled in the art.

Example 4

Use of the G2092 Allele in Varietal Selection

The G2092 allele is used in varietal selection. Genetic mixing between the resistant variety and varieties exhibiting other agronomic qualities such as high yield, high protein levels, a capacity for resistance to pre-harvest germination, makes it possible to select novel varieties which group together all the desired characters. The G2092 allele which confers resistance to *Fusarium* disease is monitored by molecular labeling during this varietal selection process.

This varietal selection scheme may also comprise the selection of varieties also comprising the allele of the CCR1 gene, called Δ3318, said allele being present in a representative sample of seeds deposited at NCIMB under the number NCIMB 41236 and/or an allele of the C4H gene, called D1938, said allele being present in a representative sample of seeds deposited at NCIMB under the number NCIMB 41507.

The invention claimed is:

1. A maize plant having an allele of the CCoAOMT2 gene, called G2092, comprising an insertion of a transposon in the last exon of the CCoAOMT2 gene, said allele being present in a representative sample of seeds deposited at NCIMB under the number NCIMB 41518.

2. The maize plant as claimed in claim 1, characterized in that it further comprises an allele of the CCR1 gene, called Δ3318, said allele being present in a representative sample of seeds deposited at NCIMB under the number NCIMB 41236; or an allele of the C4H gene, called D1938, said allele being present in a representative sample of seeds deposited at NCIMB under the number NCIMB 41507; or both.

3. A maize grain having an allele of the CCoAOMT2 gene, called G2092, comprising an insertion of a transposon in the last exon of said gene, said allele being present in the seeds deposited at NCIMB under the number NCIMB 41518.

4. The maize grain as claimed in claim 3, characterized in that it further comprises an allele of the CCR1 gene, called Δ3318, said allele being present in a representative sample of seeds deposited at NCIMB under the number CNIMB 41236; or an allele of the C4H gene, called D1938, said allele being present in a representative sample of seeds deposited at NCIMB under the number NCIMB 41507; or both.

5. A method for producing a maize plant exhibiting increased tolerance to a fungal pathogen, said maize plant comprising the introgression of the G2092 allele of the CCoAOMT2 gene, present in a representative sample of seeds deposited at NCIMB under the number NCIMB 41518, into said maize plant, said method comprising the following steps:
   a) crossing a first maize line having the G2092 allele with a second elite maize line not having said allele,
   b) genotyping the progeny obtained and selecting the descendants having the G2092 allele with the best genome ratio with regard to said second elite maize line,
   c) backcrossing said descendants with said second elite maize line which can be used for production of hybrids,
   d) repeating, if necessary, steps b) and c) until an isogenic line is obtained from said second elite maize line, having the G2092 allele, and
   e) optionally, carrying out self-fertilization in order to obtain a plant homozygous for the G2092 allele.

6. A method for producing a maize plant exhibiting increased digestibility, said maize plant comprising the introgression of the G2092 allele of the CCoAOMT2 gene, present in a representative sample of seeds deposited at NCIMB under the number NCIMB41518, into said maize plant, said method comprising the following steps:
   a) crossing a first maize line having the G2092 allele with a second elite maize line not having said allele,
   b) genotyping the progeny obtained and selecting the descendants having the G2092 allele with the best genome ration with regard to said second elite maize line,
   c) backcrossing said descendants with said second elite maize line which can be used for the production of hybrids,
   d) repeating, if necessary, steps b) and c) until an isogenic line is obtained from said second elite maize line, having the G2092 allele, and
   e) optionally, carrying out self-fertilization in order to obtain a plant homozygous for the G2092 allele.

7. The method as claimed in claim 5, characterized in that said fungal pathogen is of the genus *Fusarium*.

8. The method as claimed in claim 5, further comprising the step of introgressing the Δ3318 allele of the CCR1 gene, present in a representative sample of seeds deposited at NCIMB under the number NCIMB 41236, or the D1938 allele of the C4H gene, present in a representative sample of seeds deposited at NCIMB under the number NCIMB 41507, or both, into said maize plant.

9. A method for the preparation of a composition intended as animal feed comprising the step of preparing silage from the maize plant as claimed in claim 1.

10. The method as claimed in claim 6, further comprising the step of introgressing the Δ3318 allele of the CCR1 gene, present in a representative sample of seeds deposited at NCIMB under the number NCIMB 41236, or the D1938 allele of the C4H gene, present in a representative sample of seeds deposited at NCIMB under the number NCIMB 41507, or both, into said maize plant.

* * * * *